United States Patent

Early et al.

[11] Patent Number: 6,159,395
[45] Date of Patent: Dec. 12, 2000

[54] PROCESS AND PLANT FOR REFORMING HYDROCARBONACEOUS FEEDSTOCK

[75] Inventors: Simon Robert Early, London; Timothy Douglas Gamlin, Woking; Mark Andrew Linthwaite, Twickenham, all of United Kingdom

[73] Assignee: Kvaerner Process Technology Limited, London, United Kingdom

[21] Appl. No.: 09/117,886
[22] PCT Filed: Dec. 11, 1997
[86] PCT No.: PCT/GB97/03417
§ 371 Date: Aug. 7, 1998
§ 102(e) Date: Aug. 7, 1998
[87] PCT Pub. No.: WO98/28071
PCT Pub. Date: Jul. 2, 1998

[30] Foreign Application Priority Data

Dec. 20, 1996 [EP] European Pat. Off. .............. 96309421

[51] Int. Cl.[7] .............................. C10J 1/00; B01D 47/00
[52] U.S. Cl. .......................... 252/372; 252/373; 252/374; 252/375; 252/376; 252/377; 423/210
[58] Field of Search .................................... 252/372, 373, 252/374, 375, 376, 377; 423/210, 351–363, 644–656

[56] References Cited

U.S. PATENT DOCUMENTS

| | | | |
|---|---|---|---|
| 3,215,502 | 11/1965 | Korwin | 23/277 |
| 3,531,263 | 9/1970 | Sederquist | 48/61 |
| 3,909,299 | 9/1975 | Corrigan | 136/86 |
| 4,098,588 | 7/1978 | Buswell et al. | 48/94 |
| 4,296,085 | 10/1981 | Banquy | 423/359 |
| 4,423,022 | 12/1983 | Albano et al. | 423/360 |
| 4,681,701 | 7/1987 | Sie | 252/373 |
| 4,692,306 | 9/1987 | Minet et al. | 422/49 |
| 4,833,171 | 5/1989 | Sweeney | 518/703 |
| 4,849,187 | 7/1989 | Uozu et al. | 422/197 |
| 4,861,348 | 8/1989 | Koyama et al. | 48/94 |
| 4,909,808 | 3/1990 | Voecks | 48/94 |
| 5,106,590 | 4/1992 | Hopper et al. | 422/198 |
| 5,181,937 | 1/1993 | Karafian et al. | 48/95 |
| 5,264,008 | 11/1993 | Corrigan | 48/94 |

FOREIGN PATENT DOCUMENTS

| | | | |
|---|---|---|---|
| 0 033 128 | 8/1981 | European Pat. Off. | C01B 3/38 |
| WO 94/29013 | 12/1994 | WIPO | B01J 8/06 |

OTHER PUBLICATIONS

International Search Report, PCT/GB97/03417, Jun. 4, 1998 (4 pages).

Primary Examiner—Steven P. Griffin
Assistant Examiner—Eileen E. Nave
Attorney, Agent, or Firm—Senniger, Powers, Leavitt & Roedel

[57] ABSTRACT

The present invention provides a process for the production of a synthesis gas mixture containing carbon oxides and hydrogen from a hydrocarbon feedstock material comprising: providing a reforming zone having a plurality of chambers charged with a catalyst effective for catalysis of at least one reforming reaction; supplying to the chambers of the reforming zone a vaporous mixture of the hydrocarbon feedstock and a reforming reagent; maintaining the reforming zone under suitable reforming conditions for reforming of the hydrocarbon feedstock and reforming reagent to form the synthesis gas mixture by supplying to the reforming zone a fuel for heating the chambers by combustion and by supplying to the steam reforming zone a vaporous steam comprising combustion oxygen in which the fuel may be combusted; humidifying the vaporous steam comprising combustion oxygen; exchanging heat between the humidified vaporous steam comprising combustion oxygen entering the reforming zone and the synthesis gas mixture exiting the reforming zone; recovering from the reforming zone a cooled synthesis gas mixture; and recovering from the reforming zone a vaporous combustion products mixture comprising the products of fuel combustion in the reforming zone and any umcombusted materials supplied to the reforming zone and to a plant constructed and arranged to operate such a process.

24 Claims, 6 Drawing Sheets

FIG. 1

PRIOR ART

PROCESS AND PLANT FOR REFORMING HYDROCARBONACEOUS FEEDSTOCK

This invention relates to a process and plant for reforming hydrocarbonaceous feedstocks.

Methanol is synthesised in large volumes annually by conversion of a carbonaceous feedstock, usually a hydrocarbonaceous feedstock such as natural gas, into a mixture of carbon oxides and hydrogen. Such a mixture of gases is often referred to as synthesis gas.

The conversion of a hydrocarbon-containing feedstock, such as natural gas, into synthesis gas can be effected by steam reforming.

In a conventional steam reforming process a mixture of desulphurised hydrocarbon feedstock, such as natural gas, and steam is passed at high temperature, typically a temperature of from about 600° C. to about 1000° C., and elevated pressure, typically from about 10 bar up to about 50 bar, over a suitable reforming catalyst, such as a supported nickel catalyst. One commercially recommended catalyst which can be used for this purpose uses a mixture of calcium and aluminium oxides as support for the nickel. When natural gas is the feedstock, the principal reaction is:

$$CH_4 + H_2O \rightleftharpoons CO + 3H_2$$

The reaction products themselves are further subject to the reversible "water gas shift" reaction in which carbon dioxide and hydrogen are produced from carbon monoxide and steam:

$$CO + H_2O \rightleftharpoons CO_2 + H_2$$

A number of different types of reformer are known in the art. One such type is known as a "compact reformer" and is described in WO-A-94/29013, which discloses a compact endothermic reaction apparatus in which a plurality of metallic reaction tubes are close-packed inside a reformer vessel. Fuel is burned inside the vessel, which comprises air and fuel distribution means to avoid excessive localised heating of the reaction tubes. In a compact reformer of this type heat is transferred from the flue gas vent and from the reformed gas vent of the reformer to incoming feedstock, fuel and combustion air. Other types of reformer are not as efficient as the compact reformer in transferring heat in this way. However, many other reformer designs are known and some are described in EP-A-0033128, U.S. Pat. No. 3,531,263, U.S. Pat. No. 3,215,502, U.S. Pat. No. 3,909,299, U.S. Pat. No. 4,098,588, U.S. Pat. No. 4,692,306, U.S. Pat. No. 4,861,348, U.S. Pat. No. 4,849,187, U.S. Pat. No. 4,909,808, U.S. Pat. No. 4,423,022, U.S. Pat. No. 5,106,590 and U.S. Pat. No. 5,264,008.

In a compact reformer of the type described in WO-A-94/29013 a hydrocarbonaceous feedstock is saturated with water and preheated before entering the reaction tubes.

Fuel is burned inside the compact reformer vessel, supplying radiant and convective heat to the reaction tubes, thereby raising the temperature of the process gas inside the tubes to reforming temperatures (e.g. from about 600° C. to about 1000° C.). A reforming catalyst is charged to the tubes in this region. As the reformed gas reaches the exit end of the catalyst its temperature is from about 700° C. to about 1000° C. This gas must be cooled before downstream methanol synthesis, which desirably is conducted at a temperature below about 300° C.

In the compact reformer, combustion air supplied to the reformer is used to cool the reformed gas in the reaction tubes. Upon being cooled from, say, 850° C. to 400° C. the reformed gas passes through the Boudouard region at which dusting of the metal reformer tubes with carbonaceous deposits can occur according to the equation:

$$2CO \rightleftharpoons CO_2 + C$$

To avoid such metal dusting it is important, inter alia, to obtain the correct heat balance between the cooling combustion air and the reformed gas. A number of methods of achieving this balance are known in the art. One commercial method is to supply a larger quantity of air than is needed for combustion inside the reformer vessel. The extra mass of air cools the hot reformed gas to the desired temperature. However, this method has cost disadvantages because of the size of compressor needed to pump the excess air into the reformer. Another method is to cool the air supplied to the reformer but this is also expensive to achieve. Yet another method involves recirculating the reformed gas through the air cooler (i.e. the heat exchanger in which the incoming combustion air is used to cool the reformed gas), but this also has significant drawbacks in terms of cost and power.

Accordingly, it is an object of the present invention to provide a plant for steam reforming hydrocarbonaceous feedstocks in which the aforesaid disadvantages are minimised. It is a further object of the invention to provide such a plant in which a correct heat balance between the reformed gas and the combustion air is provided.

According to the present invention, there is provided a plant for the production of a synthesis gas mixture containing carbon oxides and hydrogen from a hydrocarbon feedstock material comprising:

a) a reforming zone, adapted to be maintained under reforming conditions, and having a plurality of chambers charged with a catalyst effective for catalysis of at least one reforming reaction, for reforming of a vaporous mixture of the hydrocarbon feedstock and a reforming reagent to form the synthesis gas mixture;

b) feedstock and reforming reagent supply means for supplying to the chambers of the reforming zone a vaporous mixture of the hydrocarbon feedstock and the reforming reagent;

c) fuel supply means for supplying to the reforming zone a suitable fuel for heating the chambers;

d) means for supplying to the reforming zone a vaporous stream comprising combustion oxygen in which the fuel can be combusted;

e) a humidification zone maintained under conditions suitable for humidifying the vaporous mixture comprising combustion oxygen;

f) a heat exchange zone adapted for exchanging heat between the reformed synthesis gas mixture and the humidified vaporous mixture comprising combustion oxygen;

g) means for recovering from the heat exchange zone a cooled synthesis gas mixture; and h) means for recovering from the reforming zone a vaporous combustion products mixture comprising the products of fuel combustion in the reforming zone and any uncombusted materials supplied to the reforming zone.

Typically, the vaporous stream comprising combustion oxygen will be air. However, it will be understood by those skilled in the art that there are many other compositions of vaporous stream comprising combustion oxygen which would be suitable in the plant of the invention. However, for convenience, combustion air will be referred to henceforth.

The plant of the invention provides the advantage that heat may be recovered adequately from the reformed synthesis gas mixture while reducing, relative to prior art reformers, the power requirements of the compressor used to compress the combustion air and without the need for recirculation apparatus to recycle the reformed synthesis gas mixture through the heat exchange zone.

The effective removal of heat from the hot reformed synthesis gas by the humidified combustion air also has the advantageous effect of reducing the size and cost of the heat exchange zone necessary to effect the heat transfer. There will always be an economic balance to be struck by the designer of a plant in accordance with the invention between the size of the heat exchange zone and the power requirements associated with pumping humidified combustion air rather than dry combustion air. This balance will be well understood by those skilled in the art.

Generally, it will be convenient for the combustion air to be humidified to a large extent, for example to a relative humidity of 80%, for instance 90% or higher, ideally close to 100%, at which point the combustion air becomes saturated with water.

Reforming reactions may be carried out with a number of suitable reagents. A preferred reagent is steam. Another convenient reagent is carbon dioxide.

Figure 1:
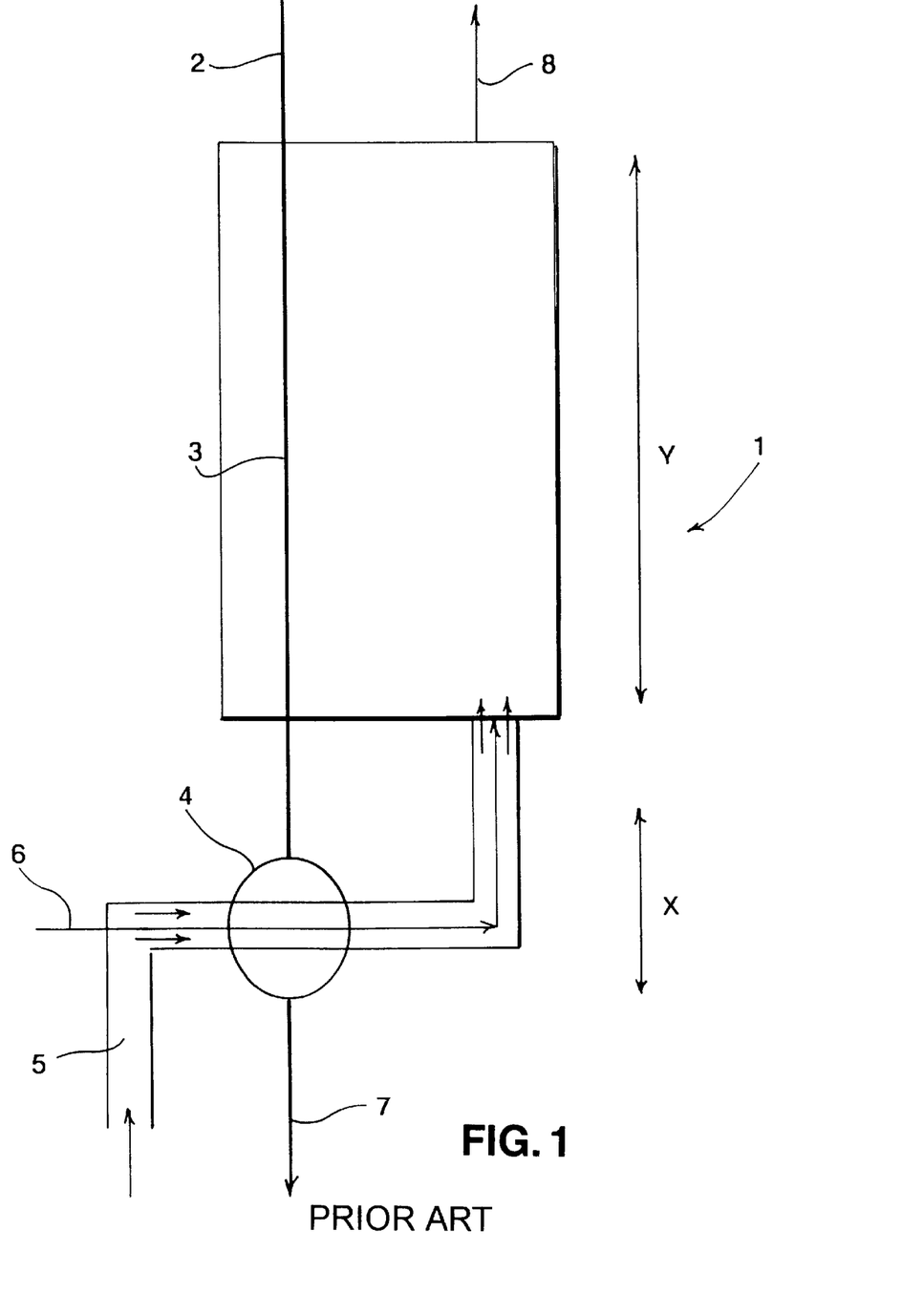
FIG. 1 is a simplified schematic diagram of a conventional reformer for illustrative purposes.

FIG. 1 shows a schematic representation of a conventional compact heat exchanging reformer, of the type described in WO-A-94/29013.

Referring to FIG. 1, there is shown a steam reforming zone 1 having two parts, X and Y. In part Y, a saturated synthesis gas production feedstock is supplied in line 2 together with steam to a plurality of chambers (not shown in FIG. 1 but represented schematically by line 3) which are charged with a suitable steam reforming catalyst such as a supported nickel catalyst, e.g. the catalyst available from ICI under the designation 57-4. Heat is supplied to line 3 by burning fuel in air in part Y of the steam reforming zone. A reformed synthesis gas mixture enters part X at a temperature of about 850° C. and is cooled in heat exchange zone 4 by incoming combustion air supplied in line 5. Fuel is supplied in line 6 and is preheated before entering part Y of the steam reforming zone by the combustion air in line 5. A cooled synthesis gas mixture is recovered in line 7. Line 8 provides an outlet for combustion gases.

A problem which commonly arises in such heat exchanging reformers concerns the heat balance in part X of the reforming zone 1. The reformed synthesis gas mixture exiting part Y must be cooled to below a specific temperature, typically 450° C., before leaving part X in order to avoid "metal dusting" of the reformer tubes and to maximise the use of heat within the reformer. In the arrangement shown in FIG. 1, the air and fuel cannot be heated above the temperature of the process gas leaving part Y. This will usually lead to an imbalance between the heat absorbed by the air and fuel and the heat required to be removed from the reformed synthesis gas. While it is possible to add excess air flow in line 5 to resolve the heat recovery imbalance, this is costly even when the air is compressed only to a modest pressure. When the air is required to be compressed to 5, 10 or 20 bar, the power requirements for additional air flow are significant.

By humidifying the air stream, when operating a plant in accordance with the invention, the total air, steam and fuel mass flow car be arranged to match the heat removal requirements of the reformed synthesis gas.

Preferably, the humidification zone comprises a vessel having a first inlet for the supply of combustion air and a second inlet for the supply of water or steam; a first outlet for recovery of a humidified combustion air stream and a second outlet for recovery of unvaporised water. The vessel may further comprise a packing material inside the vessel to increase the surface area contact between the combustion air and water inside the vessel. Such packing material may comprise one or more of Raschig rings, pall rings or saddles. However, it may not be necessary to use any packing material in some cases, for example when a spray tower saturator is used. However, it is preferred that the combustion air and the water or steam are arranged to flow countercurrently through the vessel.

The ratio of steam to air in the humidified combustion air mixture can be adjusted to a desired level by controlling the temperature of the humidification water and the pressure of the combustion air. Thus, a water temperature of 100° C. at the top of the saturator will heat the combustion air to around 96° C., giving a steam partial pressure in the humidified vapour of 0.85 bar. The steam-to-air molar and mass ratio will depend on the combustion air pressure:

| Total Pressure | Molar Ratio | Mass Ratio |
| --- | --- | --- |
| 1 bar | 5.66 | 3.50 |
| 2 bar | 0.74 | 0.45 |
| 5 bar | 0.20 | 0.13 |
| 10 bar | 0.09 | 0.06 |

The steam-to-air ratio at any given combustion air pressure is conveniently increased by increasing the humidification water temperature.

The source of heat for the humidification system will typically be low grade heat that would otherwise be rejected to the cooling system of a plant in accordance with the invention, or at best only partially recovered. Humidification water temperatures in excess of 100° C. may require recovery or a higher grade of heat, but this is still likely to be cheaper than using excess air to balance the heat recovery in the reforming zone in accordance with prior art methods.

At high steam-to-air ratios the overall consumption of water in the plant can be significant. It may therefore be desirable to provide in a plant according to the invention condensation zone for condensing water from the combusted fuel and humidified combustion air mixture. Thus the water can be recovered, along with any additional water formed by combustion of the fuel, by the use of a water wash, or dehumidification, stage. Cooling water circulating around this water recovery stage is conveniently cooled by sea water, air coolers or other suitable cooling means. Cooling water derived from a cooling tower may not be desirable because the vaporisation losses from the cooling tower can be significant and of similar magnitude to the recovered water flow.

In the case where water recovery is effected in accordance with the invention, it is preferable that the plant comprises recirculation means for recycling the condensed water to the combustion air humidification means. Even more preferably, means are provided for the recycled condensed water further to cool the recovered synthesis gas mixture. It may also be convenient to provide means for recovering unvaporised water from the humidification zone and supplying the unvaporised water as cooling water for the condensation zone.

In case the fuel or the vaporous stream comprising combustion oxygen, e.g. air, comprises any nitrogenous materials, it may be preferred that means is provided for treating the vaporous combustion products mixture to reduce the level of nitrogen-containing oxides in the gas discharged from the plant according to the invention. In the case where the vaporous combustion products mixture is condensed, it will usually also be desirable to take a purge stream from the condensed combustion products mixture to control any build up of nitrogen-containing acids in the recirculating condensed water.

In one preferred embodiment of the invention, the chambers of the steam reforming zone are close packed tubes inside the zone.

The fuel for combustion may be preheated before being supplied to the reforming zone. This may conveniently be achieved by passing the fuel through the heat exchange zone. It may be desirable to avoid over-heating the fuel by direct contact between the fuel and any heat exchange surfaces contacting the hot reformed synthesis gas mixture, at least when this is at temperatures of about 850° C. or more on exiting the reforming zone. In this case, the fuel may be contacted with heat exchange surfaces in contact cooled synthesis gas and/or with the combustion air, which is in turn heated by contact with surfaces against which the hot reformed gas is arranged to flow.

Also provided in accordance with the invention is a process for the production of a synthesis gas mixture containing carbon oxides and hydrogen from a hydrocarbon feedstock material comprising:

a) providing a reforming zone having a plurality of chambers charged with a catalyst effective for catalysis of at least one reforming reaction;

b) supplying to the chambers of the reforming zone a vaporous mixture of the hydrocarbon feedstock and a reforming reagent;

c) maintaining the reforming zone under suitable reforming conditions for reforming of the hydrocarbon feedstock and reforming reagent to form the synthesis gas mixture by supplying to the reforming zone a fuel for heating the chambers by combustion and by supplying to the steam reforming zone a vaporous stream comprising combustion oxygen in which the fuel may be combusted;

d) humidifying the vaporous stream comprising combustion oxygen;

e) exchanging heat between the humidified vaporous stream comprising combustion oxygen entering the reforming zone and the synthesis gas mixture exiting the reforming zone;

f) recovering from the reforming zone a cooled synthesis gas mixture; and g) recovering from the reforming zone a vaporous combustion products mixture comprising the products of fuel combustion in the reforming zone and any uncombusted materials supplied to the reforming zone.

Preferably, the combustion air stream is arranged to flow countercurrently to a humidification water or steam stream passing through a humidification vessel.

As discussed, it may also be desirable to include in the process the step of condensing water from the recovered combusted fuel and humidification air mixture. In this case it may also be desirable to include in the process the step of recycling the condensed water for use in saturating the combustion air. The condensed water may conveniently be recycled further to cool the recovered synthesis gas mixture.

Conveniently, the process may further comprise the step of using unvaporised combustion air humidification water as cooling water to condense water from the recovered combusted fuel and humidified combustion air mixture.

In order that the invention may be clearly understood and readily carried into effect, a number of plants constructed and arranged in accordance with the invention and designed to operate a preferred process in accordance with the invention will now be described, by way of example only, with reference to the accompanying diagrammatic drawings, in which.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

FIG. 1 has already been discussed above.

Figure 2:
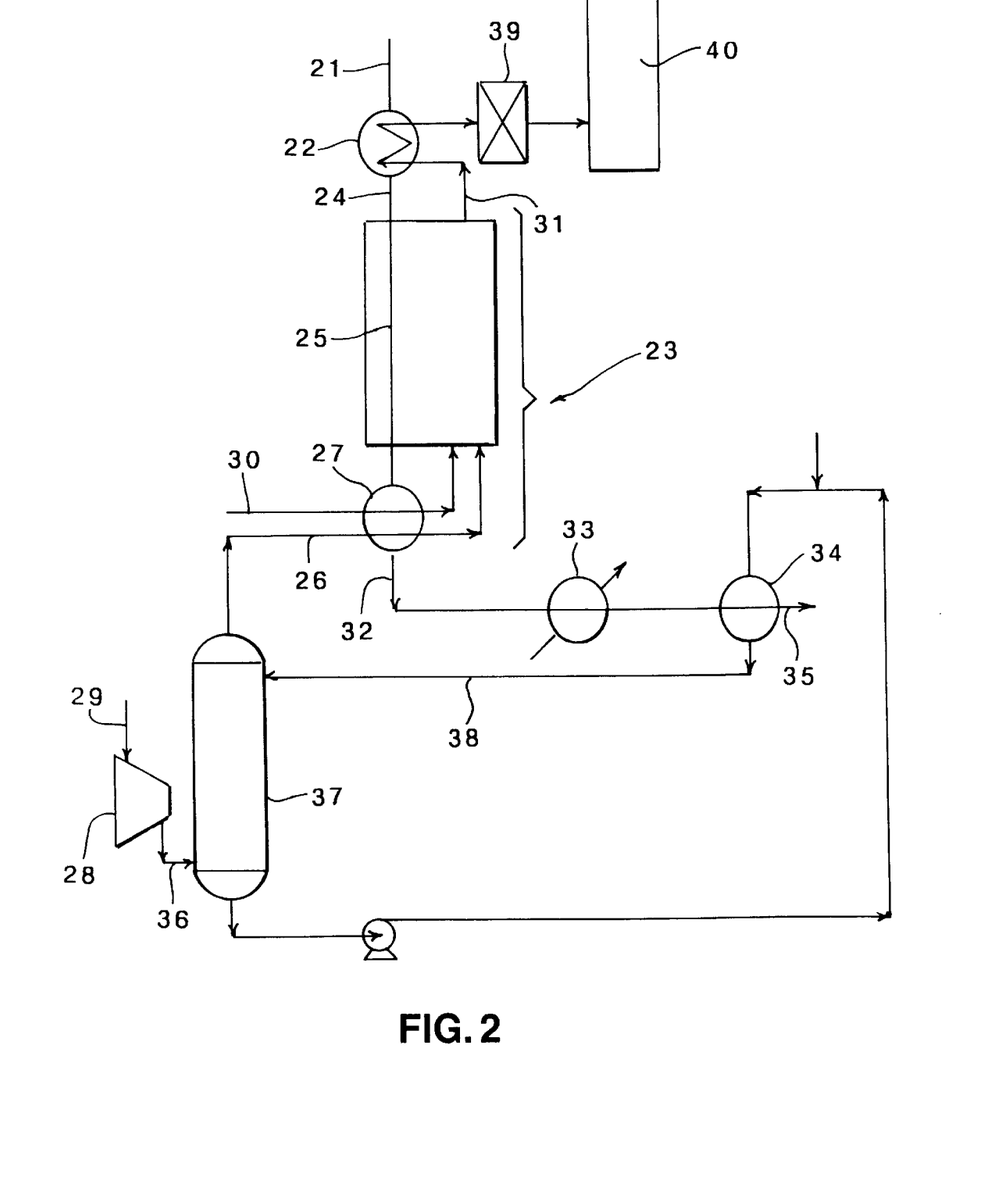
FIG. 2 is a simplified flow diagram of a first plant according to the invention.

Referring to FIG. 2, a stream of natural gas is supplied to a pre-treatment stage which is not shown in FIG. 2. For a detailed description of the pre-treatment stage, reference should be made, for example, to commonly owned, copending application Ser. No. 09/117,861, filed Aug. 7, 1998, which corresponds to International Patent Application No PCT/GB97/03413 filed Dec. 11, 1997 (Publication No. WO 98/28248) and claims priority from European Patent Application No. 96309421.4, filed Dec. 20, 1996. Briefly, the pretreatment stage involves passing the feedstock through a natural gas compressor (not shown) to compress the gas to a pressure of around 40 bar.

The compressed feedstock stream is heated to around 380° C. before passing on to a desulphurisation reactor (not shown). The natural gas feedstock contains a minor amount of sulphur as hydrogen sulphide which may be a poison to downstream catalysts in, for example, methanol synthesis. Sulphur is removed in passage through the desulphurisation reactor which contains a charge of desulphurisation materials, such as nickel molybdate and zinc oxide.

The desulphurised gas is cooled by passage through an interchanger (not shown) and flows into the bottom of a saturator column (not shown) in which the gas flows countercurrently to hot water supplied to the top of the saturator column.

In passage through the saturator column the gas mixture is saturated with water vapour. The water vapour-saturated gas mixture exists the saturator at about 200° C. and contains approximately 90° of the steam required for subsequent reforming. The gas/steam mixture is mixed with further steam supplied from a gas turbine (not shown) and passes on in line 21, referring to FIG. 2, through a mixed feed heater 22 which is mounted in the flue gas duct of reformer 23. In passage through the mixed feed heater the temperature of the gas/steam mixture is raised to about 400° C. The resulting hot gas is fed in line 24 to reformer 23.

The detail of reformer 23 is not shown in FIG. 2. The reformer is preferably of the compact type hereinbefore described and described in detail in WO-A-94/29013. Hot gas from line 24 is fed into the reaction tubes of compact reformer 23 which are packed with a suitable steam reforming catalyst, for example a supported nickel catalyst such as the catalyst available from ICI under the designation 57-4. The heat required to drive the endothermic reforming reactions is supplied by combusting a hydrogen-rich fuel inside compact reformer 23, thus transferring heat to the reaction tubes by radiation and convention. The tubes are schematically represented by line 25.

Reformer 23 is fed with hot combustion air from line 26, which is preheated in heat exchange zone 27, heated by reformed gas inside compact reformer 23, and pre-compressed in combustion air compressor 28 after being supplied to the plant in line 29. Hydrogen to fuel reformer 23 is supplied in line 30 and pre-heated in heat exchange zone 27. Hydrogen is combusted inside reformer 23, thus supplying radiant and convective heat to the reformer reaction tubes. Flue gas is vented from reformer 23 in line 31.

In compact reformer 23 the feed mixture of natural gas and recycled carbon oxides is reformed to a mixture of carbon monoxide, carbon dioxide, hydrogen and methane, a mixture commonly known as synthesis gas.

In the presence of the nickel catalyst at elevated temperatures, steam reacts with vaporous hydrocarbons at elevated temperatures and pressures to give a synthesis gas consisting of carbon dioxide, carbon monoxide, and hydrogen, together with methane and possibly other inert gases. The concentration of each constituent in the synthesis gas depends on the ratio of steam to hydrocarbon passing over the catalyst, and on the temperature and pressure at which the gases leave the catalyst. The reactions taking place are complex but the end product is determined by two reactions, i.e.

(i) the water gas shift equilibrium reaction:

$$CO + H_2O \leftrightarrows CO_2 + H_2 + Heat$$

(ii) the steam-methane equilibrium reaction:

$$Heat + CH_4 + H_2O \leftrightarrows CO + H_2$$

Overall the reactions are endothermic. A large excess of steam and a high temperature are required to move the equilibrium to the right and to reduce the residual methane content of the synthesis gas.

The synthesis gas leaves compact reformer 23 in line 32 at about 450° C. and about 30 bar.

The hot synthesis gas is further cooled through interchangers 33 and 34 and passes by way of line 35 for downstream use, for example in methanol synthesis.

Combustion air for compact reformer 23 is supplied to the plant in line 29 and passes by means of air compressor 28 into line 36 and then into an air humidifier column 37. The purpose of saturating the combustion air is to control the heat recovery inside compact reformer 23, to allow greater recovery of energy within the plant. Hot water is supplied to air humidifier column 37 in line 38. A humidified combustion air stream emerging from the top of air humidifier column 37 is supplied to reformer 23 in line 26 after cooling the reformed gas exiting reformer 23 in passage through heat exchange zone 27.

In the plant of FIG. 2, the vaporous combustion products mixture, comprising the products of fuel combustion as well as uncombusted materials supplied to the reforming zone in lines 26 and 30, is recovered in line 31 and is used to heat the incoming feedstock in interchanger 22 and is treated in nitrogen oxide treatment zone 39 before being discharged from the plant through stack 40.

Figure 3:
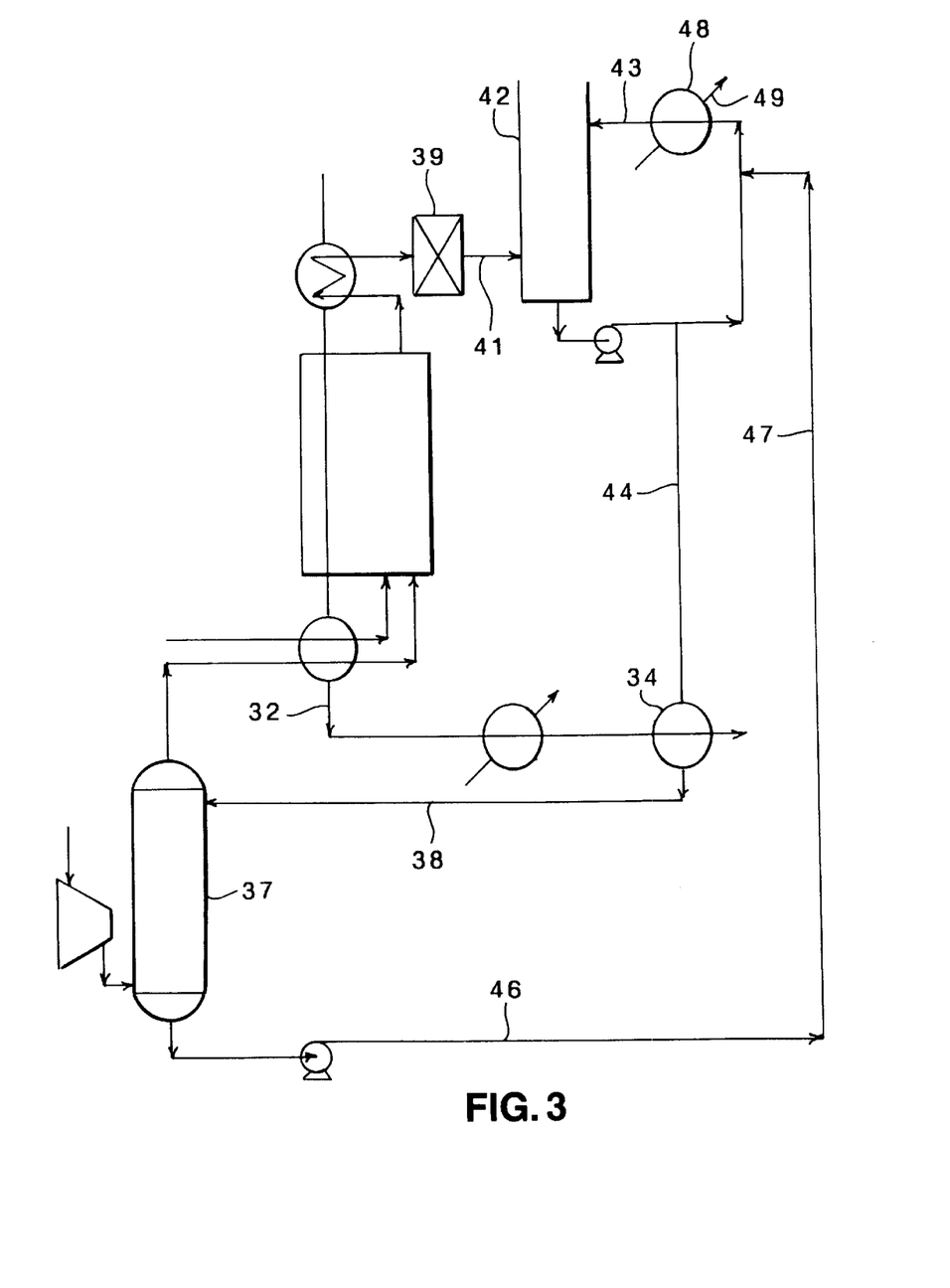
FIG. 3 is a simplified flow diagram of a second plant according to the invention.

However, it may be desirable in some cases, for example in water scarce locations, to recover the humidification water emerging from nitrogen oxide treatment zone 39. If so, the plant represented in FIG. 3 may be employed. In other respects, the plant of FIG. 3 is the same as that of FIG. 2. However, the mixture of combusted fuel and humidified combustion air from nitrogen oxide treatment zone 39 is supplied in line 41 to a desaturation zone 42 which is supplied with cooling water in line 43. Recovered water may be recycled to the combustion air humidifier 37 in lines 44 and 38. The recovered water in line 44 can also be used further to cool the reformed synthesis gas mixture in line 32 by passage through interchanger 34. Cooling water supplied in line 43 may be recycled from the bottom of combustion air humidifier 37 in lines 46 and 47 and cooled by passage through interchanger 48 which is cooled, for example, by sea water or air in line 49.

Figure 4:
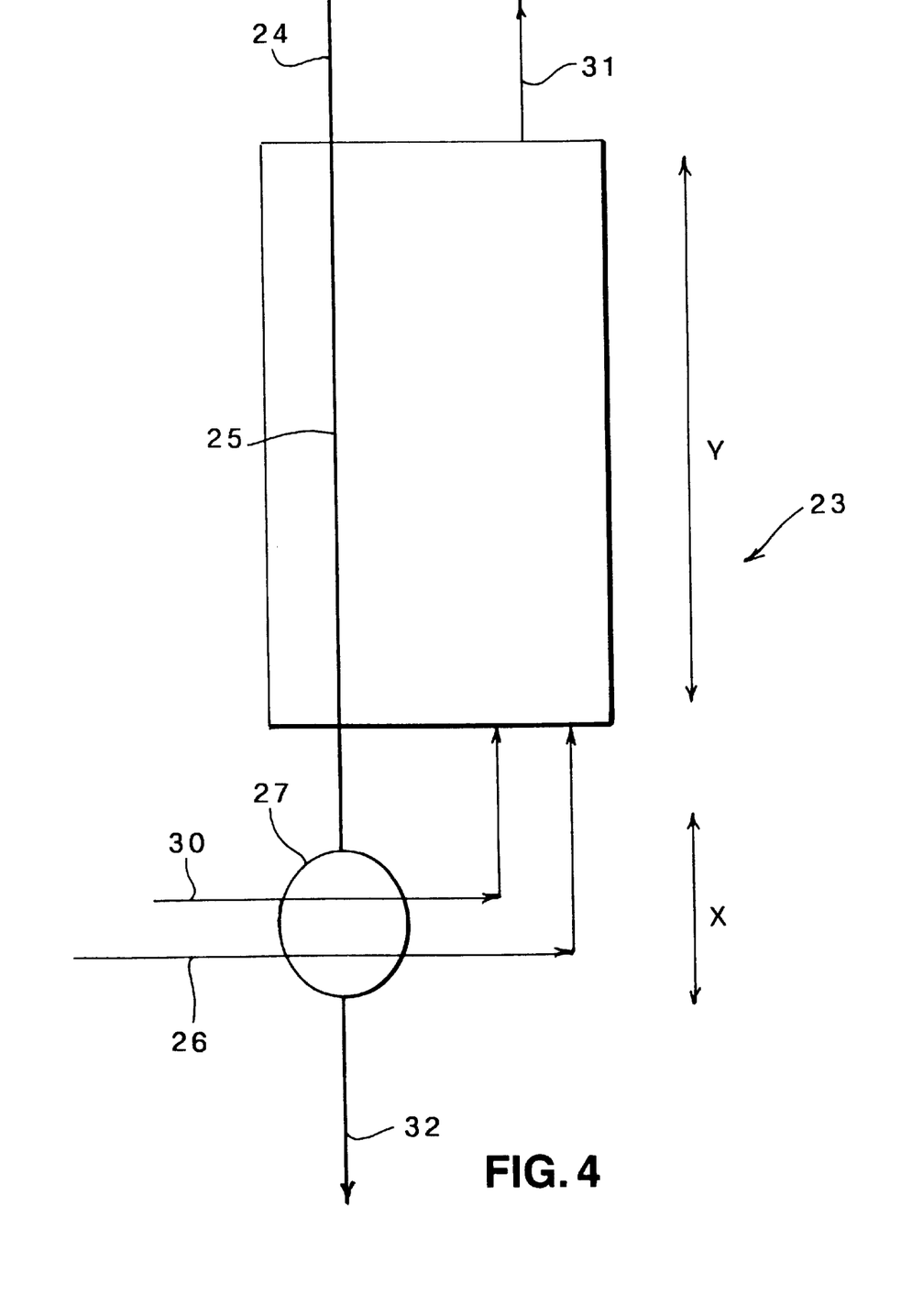
FIG. 4 is a simplified schematic view of part of a first alternative embodiment of the plants of FIGS. 2 and 3.
Figure 5:
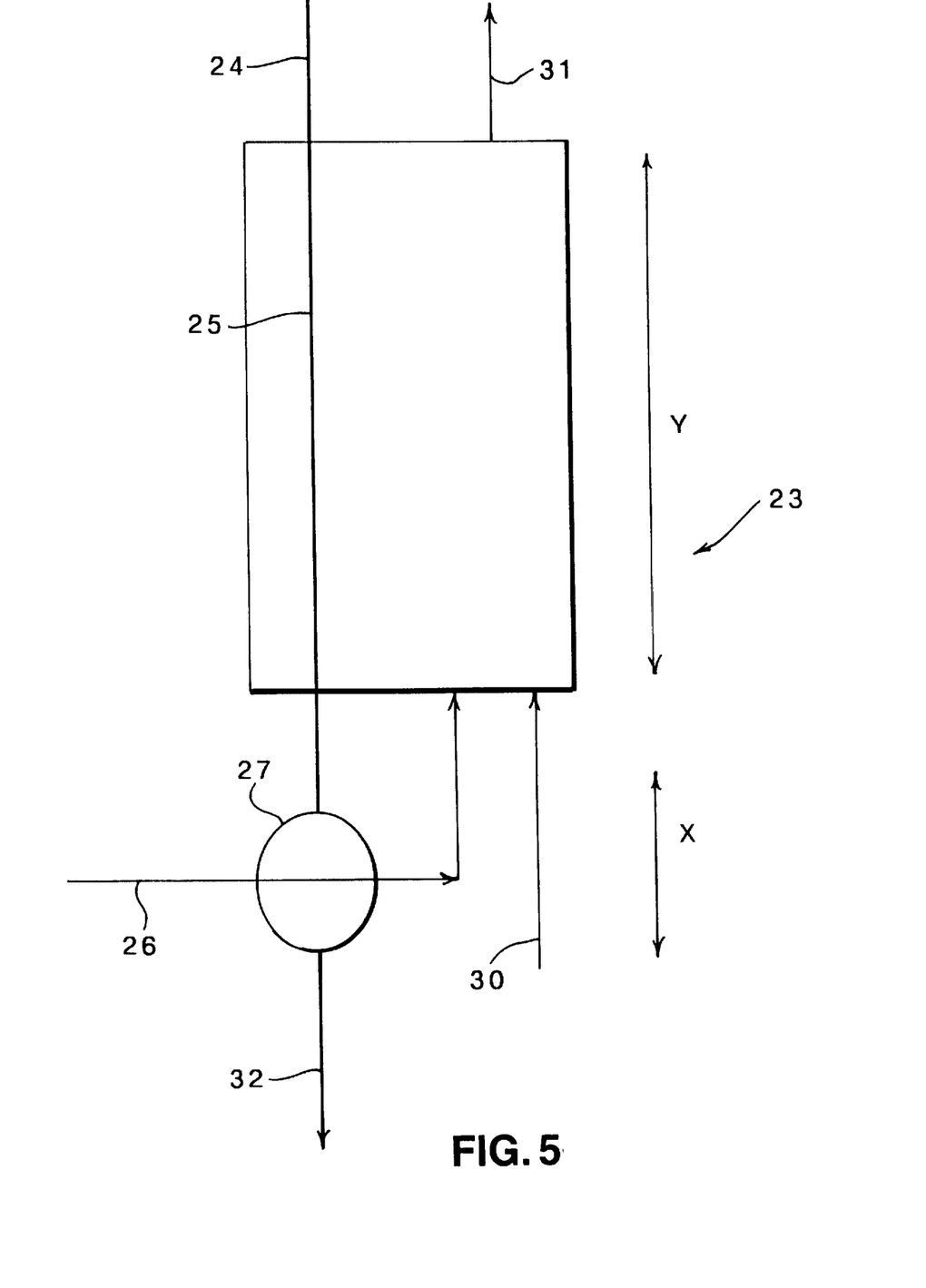
FIG. 5 is a simplified schematic view of part of a second alternative embodiment of the plants of FIGS. 2 and 3.

FIG. 4 shows an expanded view of reformer 23 of FIGS. 2 and 3. As is shown in FIG. 4, humidified combustion air is passed through heat exchange zone 27 to remove heat from the hot reformed gas exiting part Y of the reformer. In this embodiment of the invention, the fuel in line 30 is pre-heated by passage through heat exchange zone 27 and in this case the fuel is arranged to contact heat exchange surfaces inside zone 27 which are themselves in direct contact with the hot reformed gas. It may be preferable in some cases to pre-heat the fuel more gently by using the arrangement shown in FIG. 1, wherein the fuel is arranged to flow against heat exchange surfaces which are themselves in direct contact with the combustion air, but not with the hot reformed gas. Alternatively, it may be desirable not to pre-heat the fuel at all, in which case the embodiment shown in FIG. 5 may be used.

Figure 6:
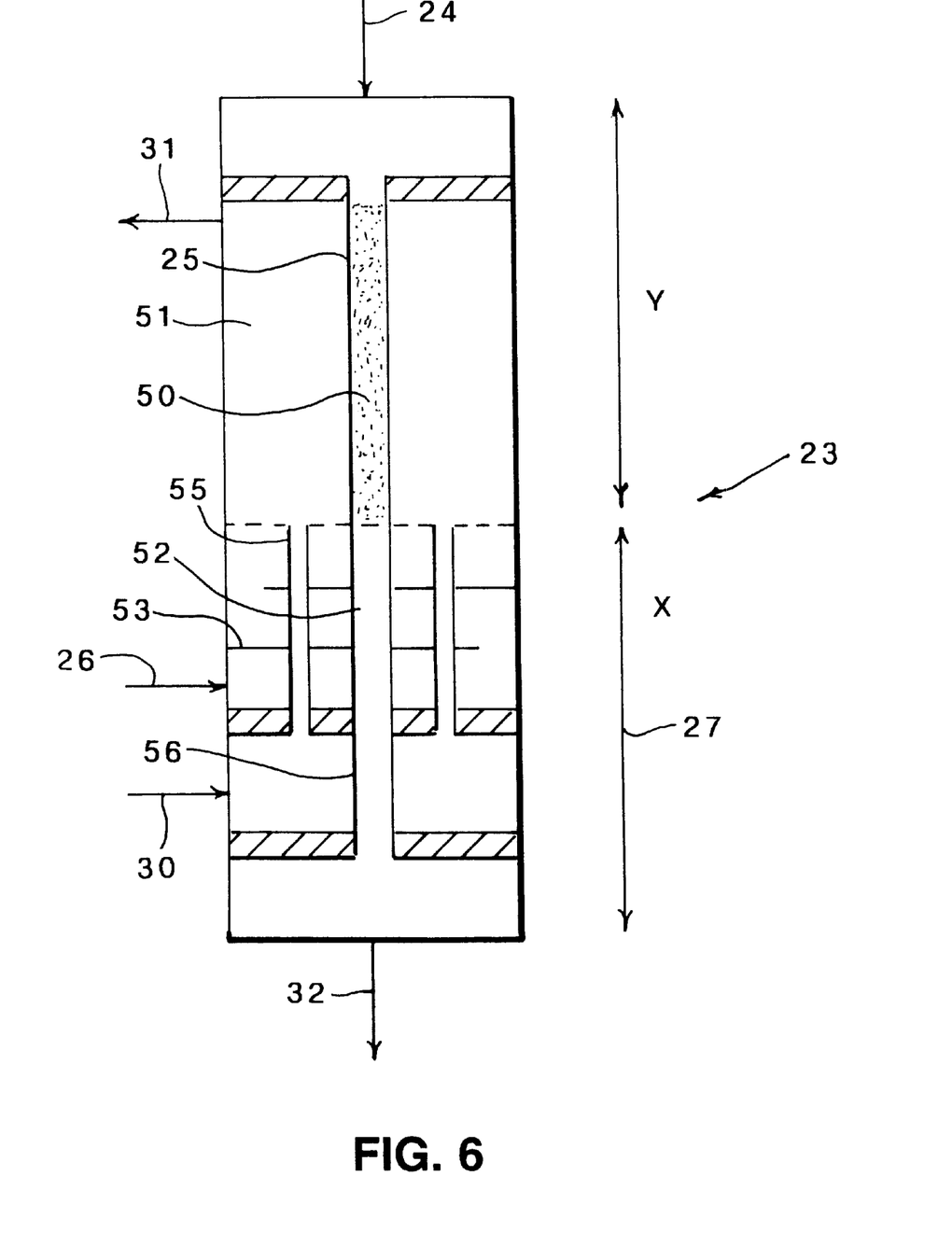
FIG. 6 is a more detailed schematic view of the part shown in FIG. 4.

In order that this may be more clearly understood, FIG. 6 shows a more detailed view of reformer 23 arranged to operate so that the fuel is pre-heated by the combustion air, as is shown schematically in FIG. 1. Referring to FIG. 6, compact reformer 23 has two parts, X and Y. Part Y represents the steam reforming zone according to the invention and part X represents the heat exchange zone according to the invention. Part Y of reformer 23 comprises a large number of close-packed reaction tubes, only one of which, tube 25, is shown in FIG. 6. Tube 25 is charged with a nickel steam reforming catalyst, such as ICI 57-4, as indicated by shaded area 50. A steam-hydrocarbon vapour mixture is supplied to reformer 23 in line 24 and passes through tube 25 which is heated by burning a mixture of hydrogen-containing fuel and saturated combustion air in area 51 surrounding tube 25.

Hot reformed synthesis gas exiting part Y of reformer 23 is cooled in heat exchange zone 27 by contact with heat exchange surface 52, against which flows a saturated combustion air stream supplied in line 26. Baffles 53 assist circulation of the humidified combustion air inside heat exchange zone 27.

Fuel is supplied in line 30 and is preheated by contact with heat exchange surface 56, against which flows a pre-cooled synthesis gas, and is then further heated by contact with heat exchange surface 55, against which flows humidified combustion air heated by exchange surface 52.

A cooled synthesis gas mixture is recovered from reformer 23 in line 32 and a vaporous combustion products mixture is recovered from reformer 23 in line 31

The use of compact reformer 23 means that much of the heat generated within the reformer is recovered internally to reduce the overall fuel requirements of the plant. Also, reformed gas and flue gas from reformer 23 is used ((in interchangers (not shown)) to heat the circulation water for the feed saturator, which is necessary if the reforming reagent is steam. The water is heated first by reformed gas in the saturator water heater, then by flue gas in the saturator water heater and finally by hot reformed gas in the saturator water heater. The arrangement depicted in FIG. 2 takes advantage of the compact reformer to provide a heat recovery system with no "heat recycle" from the methanol synthesis section to the reforming section. This makes plant start-up both easier and quicker than in conventional reformer plants.

What is claimed is:

1. A plant for the production of a synthesis gas mixture containing carbon oxides and hydrogen from a hydrocarbon feedstock material comprising:
   a) a reforming zone, adapted to be maintained under reforming conditions, and having a plurality of chambers charged with a catalyst effective for catalysis of at least one reforming reaction, for reforming of a vaporous mixture of the hydrocarbon feedstock and a reforming reagent to form the synthesis gas mixture;
   b) feedstock and reforming reagent supply means for supplying to the chambers of the reforming zone a vaporous mixture of the hydrocarbon feedstock and the reforming reagent;
   c) fuel supply means for supplying to the reforming zone a suitable fuel for heating the chambers;
   d) means for supplying to the reforming zone a vaporous stream comprising combustion oxygen in which the fuel can be combusted;
   e) a humidification zone maintained under conditions suitable for humidifying the vaporous stream comprising combustion oxygen;
   f) a heat exchange zone adapted for exchanging heat between the reformed synthesis gas mixture and the humidified vaporous stream comprising combustion oxygen;
   g) means for recovering from the heat exchange zone a cooled synthesis gas mixture; and
   h) means for recovering from the reforming zone a vaporous combustion products mixture comprising the products of fuel combustion in the reforming zone and any uncombusted materials supplied to the reforming zone.

2. A plant according to claim 1, wherein the humidification zone is adapted at least partially to saturate the vaporous stream comprising combustion oxygen with water.

3. A plant according to claim 1, wherein steam is supplied to the reforming zone as reforming reagent, the reforming zone being maintained under suitable steam reforming conditions.

4. A plant according claim 1, wherein the vaporous stream comprising combustion oxygen is air.

5. A plant according to claim 1, in which the humidification zone comprises a humidification vessel having a first inlet for the supply of the vaporous stream comprising combustion oxygen and a second inlet for supplying water or steam; a first outlet for recovery of a humidified vaporous stream comprising combustion oxygen and a second outlet for recovery of unvaporised water; and a packing material inside the vessel to increase the surface area contact between the vaporous stream comprising combustion oxygen and the water or steam inside the vessel.

6. A plant according to claim 5, wherein the packing material comprises one or more of Raschig rings, pall rings or saddles, structured packing material and sieve trays.

7. A plant according to claim 5, wherein the vaporous stream comprising combustion oxygen and the water or steam are arranged to flow countercurrently through the vessel.

8. A plant according to any one of claim 1, further comprising a condensation zone adapted for condensing water from the vaporous combustion products mixture recovered from the reforming zone.

9. A plant according to claim 8, wherein means is provided for taking a purge stream from the condensed combustion products mixture to control any build up of nitrogen containing acids in the condensed mixture.

10. A plant according to claim 8, comprising recirculation means for recycling the condensed water to the humidification zone.

11. A plant according to claim 10, wherein means are provided for the recycled condensed water further to cool the recovered synthesis gas mixture.

12. A plant according to claim 8, wherein means are provided for recovering unvaporized water from the humidification zone and supplying said unvaporized water as cooling water for the condensation zone.

13. A plant according to claim 1, wherein a nitrogen oxide treatment zone is provided for removing nitrogen oxide materials from the vaporous combustion products mixture.

14. A plant according to claim 1, wherein the chambers of the steam reforming zone are close packed tubes inside the zone.

15. A process for the production of a synthesis gas mixture containing carbon oxides and hydrogen from a hydrocarbon feedstock material comprising:
   a) providing a reforming zone having a plurality of chambers charged with a catalyst effective for catalysis of at least one reforming reaction;
   b) supplying to the chambers of the reforming zone a vaporous mixture of the hydrocarbon feedstock and a reforming reagent;
   c) maintaining the reforming zone under suitable reforming conditions for reforming of the hydrocarbon feedstock and reforming reagent to form the synthesis gas mixture by supplying to the reforming zone a fuel for heating the chambers by combustion and by supplying to the reforming zone a vaporous stream comprising combustion oxygen in which the fuel may be combusted;
   d) humidifying the vaporous stream comprising combustion oxygen;
   e) exchanging heat between the humidified vaporous stream comprising combustion oxygen entering the reforming zone and the synthesis gas mixture exiting the reforming zone;
   f) recovering from the reforming zone a cooled synthesis gas mixture; and
   g) recovering from the reforming zone a vaporous combustion products mixture comprising the products of fuel combustion in the reforming zone and any uncombusted materials supplied to the reforming zone.

16. A process according to claim 15, wherein the vaporous stream comprising combustion oxygen is humidified with water in step d).

17. A process according to claim 15, wherein steam is supplied to the reforming zone as reforming reagent, the reforming zone being maintained under suitable steam reforming conditions.

18. A process according to claim 15, wherein the vaporous stream comprising combustion oxygen is air.

19. A process according to claim 15, wherein the vaporous stream comprising combustion oxygen is arranged to flow in a humidification zone countercurrently to a humidification water or steam stream passing through the humidification zone.

20. A process according to claim 15, further comprising the step of condensing water from the recovered vaporous combustion products mixture.

21. A process according to claim 20, further comprising the step of recycling the condensed water for use in humidifying the vaporous stream comprising combustion oxygen.

22. A process according to claim 21, further comprising the step of using the condensed water being recycled further to cool the recovered synthesis gas mixture.

23. A process according to claim 20, further comprising the step of using unvaporised humidification water or steam as cooling water to condense water from the recovered vaporous combustion products mixture.

24. A process according to claim 20, further comprising the step of taking a purge stream from the condensed combustion products mixture to control any build up of nitrogenous materials in the condensed mixture.

\* \* \* \* \*